United States Patent [19]

Aschenbeck

[11] Patent Number: 4,609,628

[45] Date of Patent: Sep. 2, 1986

[54] METHOD FOR DETERMINING BINDER CONTENT AND DEGREE OF CURE IN A FIBROUS MAT

[75] Inventor: David P. Aschenbeck, Granville, Ohio

[73] Assignee: Owens-Corning Fiberglas Corporation, Toledo, Ohio

[21] Appl. No.: 574,942

[22] Filed: Jan. 30, 1984

Related U.S. Application Data

[63] Continuation-in-part of Ser. No. 374,564, May 3, 1982, abandoned.

[51] Int. Cl.[4] .................. G01J 1/10; G01N 21/75; G01N 33/44
[52] U.S. Cl. .................... 436/34; 250/339; 436/85; 436/164
[58] Field of Search .............. 250/339; 436/34, 85, 436/164; 65/4.4, 3.43, 29

[56] References Cited

U.S. PATENT DOCUMENTS

| | | | |
|---|---|---|---|
| 3,248,368 | 4/1966 | Biefeld | 436/85 X |
| 3,405,268 | 10/1968 | Brunton et al. | 250/339 |
| 3,448,268 | 6/1969 | Proctor . | |
| 3,524,983 | 8/1970 | Voelz . | |
| 3,560,179 | 2/1971 | Kleist . | |
| 3,877,818 | 4/1975 | Button et al. | 357/416 |
| 3,904,876 | 9/1975 | Arendt . | |
| 4,085,326 | 4/1978 | Williams . | |
| 4,300,049 | 11/1981 | Sturm . | |
| 4,305,659 | 12/1981 | Bilstad et al. | 356/40 |
| 4,363,968 | 12/1982 | McGowan et al. | 250/339 |

OTHER PUBLICATIONS

Myers, Journal of Applied Polymer Science, vol. 26, 747–764 (1981).
Crandall et al., Journal of Applied Polymer Science, vol. 21, 449–454 (1977).
Ealing Optics Catalog, p. 464 (no date given).
Kendall, D. N., Ed., *Applied Infrared Spectroscopy*, Reinhold Publishing Corp., New York, N.Y., 1966, pp. 5 and 262–267.
Military Standardization Handbook, Glass MIL–HDBK–722 (MR), Aug. 1969, pp. 30 and 31.
Brunton, D. C., "Measurement of Moisture in the Paper Industry", *Southern Pulp and Paper Manufacturer*, May 10, 1967, pp. 108, 109, 114, 116, 117.
Brunton, D. C., "On–Machine Measurement of Coating", paper presented to the *TAPPI* 20th Coating Conference on May 25–29, 1969, Minneapolis, Minnesota, pp. 1–5.
Van Horne, W. E., "Measurement and Control of Coextruded Coatings by Infrared", paper distributed at Oct., 1974 *TAPPI Testing/Paper Synthetics Conference*, pp. 35–39.
Wu, Yao–Man and Huang, Zhi–Tang, "Study of the Curing Process for Resole–Type Phenol–Formaldehyde Resins by Infrared Spectroscopy", *Gaofenzi Tongxun*, No. 6, Dec., 1981, pp. 403–407 (translation included).
Young, R. H. and Kopf, P. W. & Salgado, O., "Curing Mechanism Of Phenolic Resins", *TAPPI* 1980 *Paper Synthetics Conference*, pp. 229–234.
Brunton, D. C., "Moisture and Basis Weight Measured by Infrared", *Paper Trade Journal*, Apr. 15, 1968, pp. 63 and 64.
Gardner, R. C., "Moisture/Basis Weight Infrared Gage for Paper", *Instrumentation Technology*, Jan., 1968, pp. 51–54.
Overhoff, M. W., "Infrared Gages—Their Use, Deficiencies and Applications for On–Line Control", *TAPPI*, vol. 56, No. 2, Feb. 1973, pp. 70–73.

*Primary Examiner*—Arnold Turk
*Attorney, Agent, or Firm*—Ronald C. Hudgens; Ted C. Gillespie

[57] ABSTRACT

A method for measuring binder characteristics in a mat of binder coated mineral fibers, the binder having a first cure indicator constituent, the amount of which changes at a first rate as the binder is cured, and a second cure indicator constituent, the amount of which changes at a second rate, different from the first rate, as the binder is cured, comprising radiating the mat and binder with first, second, third and fourth wavelengths of electromagnetic radiation, the first wavelength being absorbed by the binder including the first cure indicator constituent, the second wavelength being a reference for the first wavelength and being not absorbed by the binder or the cure indicator constituents, the third wavelength being absorbed by the binder including the second cure indicator constituent, and the fourth wavelength being a reference for the third wavelength and being not absorbed by the binder or the cure indicator constituents, and further sensing the amount of energy of the first, second, third and fourth wavelengths transmitted through the mat and the binder, and, finally determining the degree of cure and/or the amount of binder from the sensed energies.

12 Claims, 7 Drawing Figures

METHOD FOR DETERMINING BINDER CONTENT AND DEGREE OF CURE IN A FIBROUS MAT

This is a continuation-in-part of Ser. No. 374,564, filed May 3, 1982 and now abandoned.

TECHNICAL FIELD

This invention pertains to the measuring of a binder dispersed in a mat of fibrous material, such as a mat of glass fibers. In one of its more specific aspects, this invention relates to measuring the amount of binder on the fibers. In another of its more specific aspects, this invention relates to measuring the degree or extent of cure of the binder material on the fibers.

BACKGROUND OF THE INVENTION

A common practice in manufacturing products containing fibrous material, such as manufacturing mats or packs of mineral material, is to apply a binder material to the fibers, thereby connecting the fibers with each other and giving structure and resiliency to the product. In the manufacture of mats of mineral fibers, a preferred binder is an organic binder, such as a phenol-formaldehyde urea binder. Phenol-formaldehyde urea binders have been found to be particularly useful in the manufacture of glass fiber mats for such uses as insulation products.

In the manufacture of mineral fiber mats having a binder thereon, it is usually necessary to subject the mat and binder to a curing oven to advance the binder to a cured or set state. One off the problems associated with passing mineral fiber mats through curing ovens is that there is a certain lack of control over the process, i.e., the product is often either undercured or overcured. Attempts have been made to measure, during the production process, the amount of binder on the mats and the extent to which the binder has been cured, but previous attempts were not sufficiently accurate for process control purposes.

A previous method for measuring characteristics of a mat of fibers as disclosed in U.S. Pat. No. 4,363,968, to McGowan et al., including radiating the mat with electromagnetic radiation having different wavelengths with each wavelength being absorbed (or not absorbed) by various components of the mat and binder. By choosing infrared radiation which is absorbed by the binder, and measuring the transmission of the radiation through the pack, an indication of the amount of binder present is obtained. In practice, two wavelengths of infrared radiation have been used, one which is absorbed by the binder and one which is unaffected by the binder. Taking the ratio of the two gives a signal related to the binder content. For example, a first energy which is absorbed by the binder and a reference energy, which is not absorbed by the binder, could both be directed toward the mat. A simple comparison of the sensed energies transmitted through the mat and the binder would disclose the relative amount of the first energy absorbed and thereby disclose the amount of binder on the mat.

Such a prior art method is deficient, however, in that the amount of the energy absorbed by the binder is not only a function of the amount of binder present within the pack, but also upon the degree of cure or advancement of the organic binder toward a cured state. It is not always possible to find an energy with a wavelength which is insensitive to the degree of cure. Thus, there is a need for a method for measuring binder characteristics in a mat of binder-coated mineral fibers which takes into account the effect of the degree of cure on the measurement of the amount of binder in the mineral fiber pack.

SUMMARY OF THE INVENTION

According to this invention, there is provided a method for measuring binder characteristics in a mat of binder-coated mineral fibers, the binder having a first cure indicator constituent, the amount of which changes at a first rate as the binder is cured, and a second cure indicator constituent, the amount of which changes at a second rate, different from the first rate, as the binder is cured, comprising radiating the mat and the binder with first, second, third and fourth wavelengths of electromagnetic radiation, where the first wavelength is absorbed by the binder including the first cure indicator constituent, the second wavelength is a reference for the first wavelength and is substantially not absorbed by either the binder or the first or second cure indicator constituents, the third wavelength is absorbed by the binder including the second cure indicator constituent, and the fourth wavelength is a reference for the third wavelength and is substantially not absorbed by either the binder or the first or second cure indicator constituents, and further sensing the energy of the first, second, third and fourth wavelengths transmitted through the mat and the binder, and, finally, determining the degree of cure of the binder from the sensed energies. By using energies of two different wavelengths (the first and third wavelength, above), each of which is sensitive to the degree of cure, but at different rates, and comparing them on a calibrated basis with each other, one can determine the actual degree of cure of the binder.

In one embodiment of the invention, the degree of cure is determined from the sensed energies according to the equation:

$$\text{Degree of Cure} = A + \left[ \frac{1 - B}{1 - B \frac{f(c/d)}{f(a/b)}} - 1 \right] B'$$

where a, b, c and d, respectively, are the sensed energies of the first, second, third and fourth wavelengths transmitted through the mat and the binder A, B and B' are calibration constants, and f(x), f(a/b) or f(c/d), is the ratio of transmitted energies suitably modified to be proportional to the amount of binder and cure indicator constituent (a or c) on the mat.

In a specific embodiment of the invention, the amount of either the first or the second cure indicator constituents increases upon an increase in the degree of cure, and the amount of the other cure indicator constituent decreases upon an increase in the degree of cure.

In a preferred embodiment of the invention, at least one of the first and third energies has a wavelength selected from the following group of wavelengths:

| Wavelength (Microns) | Constituent |
| --- | --- |
| 2.52 | OH |
| 2.35 | C—H |
| 2.28 | C—H |
| 2.16 | Aromatic C—H |
| 1.93 | Water |

-continued

| Wavelength (Microns) | Constituent |
| --- | --- |
| 1.75 | C—H |
| 1.69 | C—H |
| 1.56 | OH |
| 1.45 | OH |

In a more preferred embodiment of the invention, the binder comprises a phenol-formaldehyde urea resin.

In yet another embodiment of the invention, the second wavelength equals the fourth wavelength, i.e., one reference wavelength is used for both cure indicator constituents.

According to this invention, there is also provided a method for measuring binder characteristics in a mat of binder-coated mineral fibers, the binder having a first cure indicator constituent, the amount of which changes at a first rate as the binder is cured, and a second cure indicator constituent, the amount of which changes at a second rate, different from the first rate, as the binder is cured, comprising radiating the mat and the binder with electromagnetic radiation having first, second, third and fourth wavelengths, where the first wavelength is absorbed by the binder including the first cure indicator constituent, the second wavelength is a reference for the first wavelength and is substantially not absorbed by either the binder or the first or second cure indicator constituents, the third wavelength is absorbed by the binder including the second cure indicator constituent, and the fourth wavelength is a reference for the third wavelength which is substantially not absorbed by either the binder or the first or second cure indicator constituents, and further sensing the energy of first, second, third and fourth wavelengths transmitted through the mat and the binder, and determining the amount of the binder from the sensed energies. By using energies of two different wavelengths (the first and third wavelengths, above), each of which is sensitive to the degree of cure, but at different rates and comparing them on a calibrated basis with each other, one can determine the actual amount of binder.

In a specific embodiment of the invention, the amount of binder is determined from the sensed energies according to the equation $$\text{Amount of Binder} = C[f(a/b) + D[f(c/d)]$$

where a, b, c and d are the sensed energies of the first, second, third and fourth wavelengths, respectively, transmitted through the mat and the binder, C and D are calibration constants, and f(x) is the ratio of transmitted energies suitably modified to be proportional to the amount of binder and cure indicating constituent (a or c) on the mat.

DESCRIPTION OF THE INVENTION

This invention will be described in terms of a method for measuring characteristics of a phenolic binder on a glass fiber mat, although it is to be understood that the invention can be practiced on mats of other heat-softenable mineral material such as rock, slag and basalt, and in conjunction with other binders besides phenolic binders.

Figure 1:
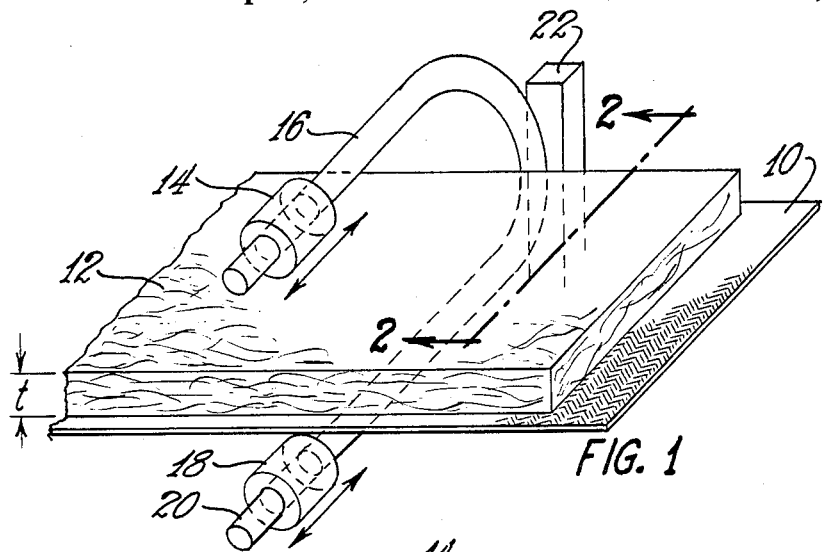
FIG. 1 is a schematic view in perspective of the apparatus for measuring binder characteristics according to the method of the present invention.
Figure 2:
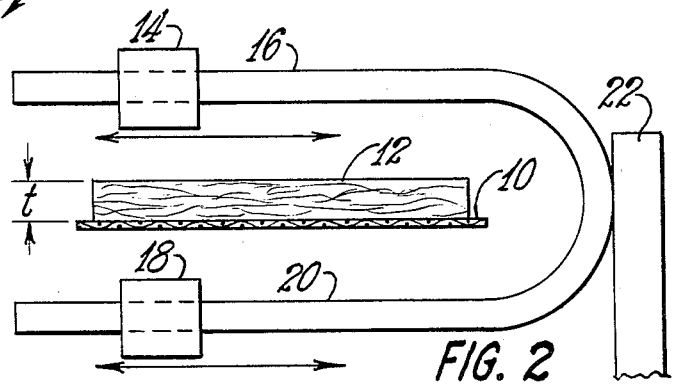
FIG. 2 is a schematic cross section in elevation along line 2—2 of FIG. 1.

As shown in FIGS. 1 and 2, conveyor 10 transports mat 12 past the apparatus for measuring the binder characteristics. Positioned above the conveyor is transmitter 14 for radiating the mat and the binder with electromagnetic radiation having the various wavelengths. The transmitter can be of any type suitable for directing energy having specified wavelengths in a specified direction. A HEMI IR Sensor transmitter manufactured by AccuRay Corporation, Columbus, Ohio, has been found to be an acceptable transmitter. Preferably the wavelengths of the electromagnetic radiation transmitted by the transmitter are in the infrared range, and each reference wavelength is preferably very closely associated with its cure indicator constituent wavelength. The transmitter can be mounted on a suitable member, such as transmitter beam 16, and the transmitter can be mounted for oscillatory movement, by means not shown, across the width of the pack in a direction transverse to the machine direction of the conveyor.

Positioned beneath the conveyor is receiver 18, which is adapted to receive or sense the energy of the various wavelengths transmitted by the transmitter. The receiver can be of any type suitable for receiving and sensing the energy transmitted by the transmitter, and must be capable of differentiating between the various wavelengths of the transmitting energies. A HEMI IR Sensor receiver manufactured by AccuRay Corporation, Columbus, Ohio, has been found to be an acceptable receiver. The receiver can be mounted on any suitable member such as receiver beam 20, and the receiver can be adapted with means, not shown, for oscillating the receiver back and forth across the width of the pack, in conjunction with the transmitter. The receiver beam and transmitter beam can be mounted on any suitable support, such as support post 22.

The four transmitted energies, which can be labeled a, b, c and d, respectively, are transmitted by the transmitter and received by the receiver. Preferably, a, b, c, and d have wavelengths within the range of from about 1.3 to about 3.0 microns. Also, preferably, each of the reference energies b and d has a wavelength very close to its cure indicator constituent energy a and c, respectively. It is possible that b and c could have identical wavelengths, and thus there would be only one energy serving as the reference energy for both cure indicator constituents.

Preferably, the binder is a phenol-formaldehyde urea resin, and the cure indicator constituents are selected so that the first or third energies have wavelengths selected from the following group of wavelengths:

| Wavelength (Microns) | Constituent |
| --- | --- |
| 2.52 | OH |
| 2.35 | C—H |
| 2.28 | C—H |
| 2.16 | Aromatic C—H |
| 1.93 | Water |
| 1.75 | C—H |
| 1.69 | C—H |
| 1.56 | OH |
| 1.45 | OH |

The preferred wavelength choices are as follows:
$\lambda a = 2.25$ microns (increases as cure advances)
$\lambda b = 1.85$ microns (reference for $\lambda a$)
$\lambda c = 2.16$ microns (decreases as cure advances)
$\lambda d = 1.85$ microns (reference for $\lambda c$)

Figure 3:
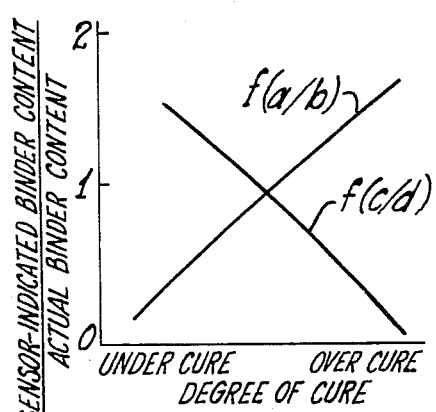
FIG. 3 is a graph of the effect of two cure indicator constituents on the sensed binder contents in a case where one of the cure indicator constituents increases with the degree of cure, and the other cure indicator constituent decreases with the degree of cure.

As shown in FIG. 3, the graph of the suitably modified ratio of the first cure indicator constituent to its reference wavelength (i.e., a/b) increases with the degree of cure. The plot of the second cure indicator constituent to its reference wavelength (i.e., c/d) has a negative slope since c represents a cure indicator constituent which decreases as cure is advanced. Thus, the slopes of the two curves do not have the same sign.

Figure 4:
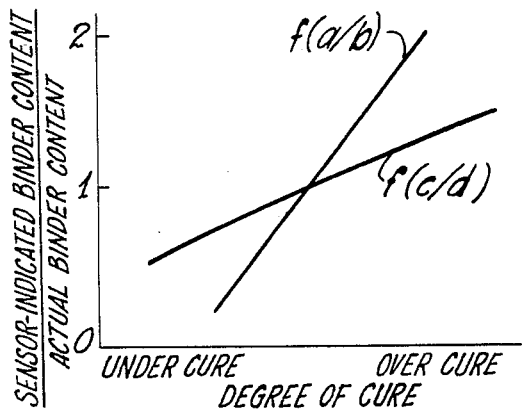
FIG. 4 is a graph of the effect of two cure indicator constituents of the sensed binder contents in a situation where both of the cure indicator constituents increase with the degree of cure, but at different rates.

As shown in FIG. 4, the slopes of the two cure indicator constituents can have the same sign, as long as the slopes are different. Since the slopes are different, the two cure indicator constituents, a and b, change at different rates with a change in the degree of cure.

In determining the degree of cure from the sensed energies it has been found useful to use the following equation:

$$\text{Degree of Cure} = A + \left[ \frac{1 - B}{1 - B \frac{f(c/d)}{f(a/b)}} - 1 \right] B',$$

where a, b, c and d are the sensed energies of the first, second, third and fourth wavelengths, respectively, transmitted through the mat and the binder, A and B and B' are calibration constants, and f(x) is the ratio of transmitted energies suitably modified to be proportional to the amount of binder and cure indicating constituent (a or c) on the mat.

Also, it has been found useful in determining the amount of binder on the pack to use the following equation: Amount of Binder $= C[(f(a/b) + D[f(c/d)]$, where a, b, c and d are the sensed energies of the first, second, third and fourth wavelengths, respectively, transmitted through the mat and the binder, C and D are calibration constants, and f(x) is the ratio of transmitted energies suitably modified to be proportional to the amount of binder and cure indicating constituent (a or c) on the mat.

Figure 5:
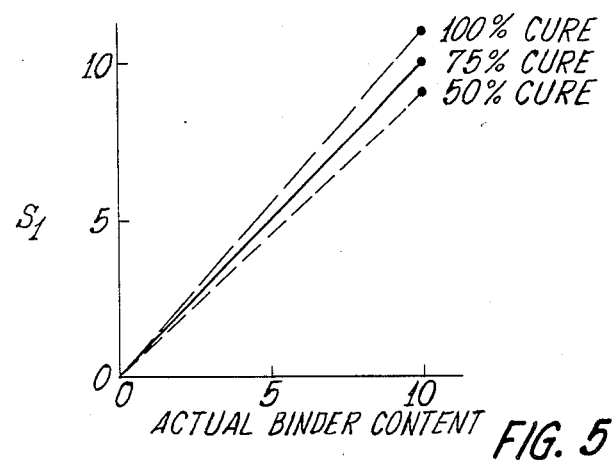
FIGS. 5 and 6 are graphs of families of curves indicating the sensed binder content as a function of the actual binder content for the two cure indicator constituents, respectively.
Figure 6:
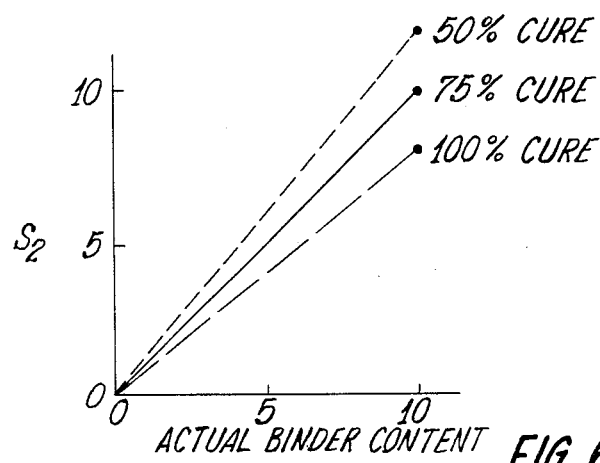

For example, f(a/b) can be of the form $-\log (a/b)$ where a/b is the ratio of energies transmitted through the pack and sensed for the first and second energies, a and b, respectively. The sensor measurements of binder would then be:

$$S_1 = b_1 - m_1 \log (a/b)$$

and $$S_2 = b_2 - m_2 \log (c/d)$$

where $b_1$, $b_2$, $m_1$ and $m_2$ are constants such that $S_1$ and $S_2$ are in the desired binder content units (such as grams/ft.$^2$, for example). $S_1$ and $S_2$ are expressions of calibrated sensor output from the sensed energies a, b, c, and d. $S_1$ and $S_2$ each represent an amount of binder on the pack, but each is biased by cure. The graphs $S_1$ and $S_2$ are shown in FIGS. 5 and 6, respectively. The families of curves shown in FIGS. 5 and 6 show that $S_1$ increases with cure, and $S_2$ decreases with cure.

Figure 7:
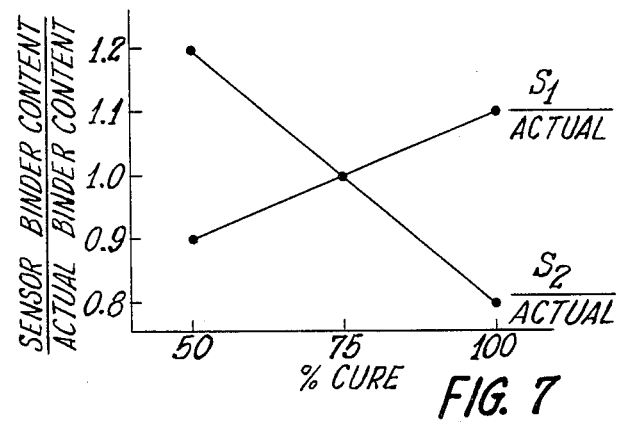
FIG. 7 is a graph of the sensed-to-actual binder content as a fraction of degree of cure.

These relationships can be simplified by replotting as shown in FIG. 7. This plot shows the slope of the sensor-vs-actual correlation for each level of cure. FIG. 7 merely illustrates a specific example of the general relationships shown in FIG. 3.

From the information in FIG. 7, the relationships of amount of binder and degree of cure can be determined as follows:

$$\text{amount of binder} = \frac{S_1 - \frac{\gamma_1}{\gamma_2} S_2}{1 - \frac{\gamma_1}{\gamma_2}}$$

$$\text{degree of cure} = A + \left[ \frac{1 - \frac{\gamma_1}{\gamma_2}}{1 - \frac{\gamma_1}{\gamma_2} \frac{S_2}{S_1}} - 1 \right] \frac{1}{\gamma_1}$$

where $\gamma_1$ is the slope of the ratio ($S_1$/actual) vs cure in FIG. 7, $\gamma_2$ is the slope of the ratio ($S_2$/actual) vs cure in FIG. 7, and A is the calibration constant. As can be seen by referring to the general form of the equations, $\gamma_1/\gamma_2$ is the constant B, and $1/\gamma_1$ is the constant B'.

EXAMPLE

Assume nominal cure is arbitrarily set at a convenient reference point, such as 75% cure. Thus A equals 75. Assume the slope $\gamma_1$ equals 0.004 and the slope $\gamma_2$ equals $-0.008$. $\gamma_1$ and $\gamma_2$ would be determined from the actual results of the chosen energies a, b, c and d. In practice, calibration data from a large number of samples of varying binder content and cure are plotted as in FIGS. 5 and 6, and combined as in FIG. 7, yielding $\gamma_1$ and $\gamma_2$, as can be appreciated by those skilled in the art. Then $$\text{amount of binder} = \frac{S_1}{1.5} + \frac{S_2}{3.0}$$

and $$\text{degree cure} = 75 + \left[ \frac{1.5}{1 + .5(S_2/S_1)} - 1 \right] 250$$

The method of this invention can be employed to continuously monitor the amount of binder on the mat and the degree of cure of the binder, and to provide such information in any form suitable for other process controls such as oven controls, pack-forming controls, and fiber-forming controls.

It will be evident from the foregoing that various modifications can be made to this invention. Such, however are considered as being within the scope of the invention.

INDUSTRIAL APPLICABILITY

This invention will be found to be useful in the manufacture of packs of mineral fibers for such uses as glass fiber thermal insulation products and glass fiber acoustical insulation products.

I claim:

1. A method for determining the degree of cure in a mat of binder-coated mineral fibers, said binder having a first cure indicator constituent, the amount of which changes at a first rate as said binder is cured, and a second cure indicator constituent, the amount of which changes at a second rate, different from said first rate, as said binder is cured, comprising:

(a) radiating said mat and said binder with first, second, third and fourth wavelengths of electromagnetic radiation;
   said first wavelength being absorbed by said binder including said first cure indicator constituent;
   said second wavelength being a reference for said first wavelength and being substantially not absorbed by either said binder or said first or second cure indicator constituents;
   said third wavelength being absorbed by said binder including said second cure indicator constituent;
   said fourth wavelength being a reference for said third wavelength and being substantially not absorbed by either said binder or said first or second cure indicator constituents;

(b) sensing the amount of energy of said first, second, third and fourth wavelengths transmitted through said mat and said binder;

(c) determining a first cure-biased value for the amount of binder on said mat from the sensed energy of said first and second wavelengths, and determining a second cure-biased value for the amount of binder on said mat from the sensed energy of said third and fourth wavelengths; and (d) determining the degree of cure of said binder from said first and second cure-biased values.

2. The method of claim 1 comprising determining the degree of cure from the sensed energies according to the following equation $$\text{Degree of Cure} = A + \left[ \frac{1 - B}{1 - B\frac{f(c/d)}{f(a/b)}} - 1 \right] B'$$

where a, b, c and d are the sensed energies of said first, second, third and fourth wavelengths, respectively, transmitted through said mat and said binder, A, B, and B' are calibration constants, and f(a/b) and f(c/d) are ratios of transmitted energies suitably modified to be proportional to the amount of binder and cure indicator constituent (a or c) on the mat.

3. The method of claim 1 in which the amount of one of said cure indicator constituents increases upon an increase in the degree of cure, and the amount of the other of said cure indicator constituents decreases upon an increase in the degree of cure.

4. The method of claim 1 in which at least one of said first and third energies have wavelengths selected from the following group of wavelengths:

| Wavelength (Microns) | Constituent |
| --- | --- |
| 2.52 | OH |
| 2.35 | C—H |
| 2.28 | C—H |
| 2.16 | Aromatic C—H |
| 1.93 | Water |
| 1.75 | C—H |
| 1.69 | C—H |
| 1.56 | OH |
| 1.45 | OH |

5. The method of claim 4 in which said binder comprises a phenol-formaldehyde urea resin.

6. The method of claim 1 in which said second wavelength equals said fourth wavelength.

7. A method for determining the amount of binder in a mat of binder-coated mineral fibers, said binder having a first cure indicator constituent, the amount of which changes at a first rate as said binder is cured, and a second cure indicator constituent, the amount of which changes at a second rate, different from said first rate, as said binder is cured, comprising:

(a) radiating said mat and said binder with electromagnetic radiation having first, second, third and fourth wavelengths;
   said first wavelength being absorbed by said binder including said first cure indicator constituent;
   said second wavelength being a reference for said first wavelength and being substantially not absorbed by either said binder or said first or second cure indicator constituents;
   said third wavelength being absorbed by said binder including said second cure indicator constituent;
   said fourth wavelength being a reference for said third wavelength and being substantially not absorbed by either said binder or said first or second cure indicator constituents;

(b) sensing the amount of energy of said first, second, third and fourth wavelengths transmitted through said mat and said binder;

(c) determining a first cure-biased value for the amount of binder on said mat from the sensed energy of said first and second wavelengths, and determining a second cure-biased value for the amount of binder on said mat from the sensed energy of said third and fourth wavelengths; and (d) determining the amount of said binder from said first and second cure-biased values.

8. The method of claim 7 comprising determining the amount of binder from the sensed energies according to the following equation $$\text{Amount of Binder} = C[f(a/b)] + D[f(c/d)]$$

where a, b, c and d are the sensed energies of said first, second, third and fourth wavelengths, respectively, transmitted through said mat and said binder, C and D are calibration constants, and f(a/b) and f(c/d) are ratios of transmitted energies suitably modified to be proportional to the amount of binder and cure indicator constituent (a or c) on the mat.

9. The method of claim 7 in which the amount of one of said cure indicator constituents increases upon an increase in the degree of cure, and the amount of the other of said cure indicator constituents decreases upon an increase in the degree of cure.

10. The method of claim 7 in which at least one of said first and third energies have wavelengths selected from the following group of wavelengths:

| Wavelength (Microns) | Constituent |
| --- | --- |
| 2.52 | OH |
| 2.35 | C—H |
| 2.28 | C—H |
| 2.16 | Aromatic C—H |
| 1.93 | Water |
| 1.75 | C—H |
| 1.69 | C—H |
| 1.56 | OH |
| 1.45 | OH |

11. The method of claim 10 in which said binder comprises a phenol-formaldehyde urea resin.

12. The method of claim 7 in which said second wavelength equals said fourth wavelength.

* * * * *